United States Patent
Wasson et al.

(10) Patent No.: US 10,918,289 B1
(45) Date of Patent: Feb. 16, 2021

(54) RING FOR OPTICALLY MEASURING BIOMETRIC DATA

(71) Applicant: Fitbit, Inc., San Francisco, CA (US)

(72) Inventors: Jaclyn Leverett Wasson, Alameda, CA (US); Peter W. Richards, San Francisco, CA (US); Lindsey Michelle Sunden, San Francisco, CA (US); Corey Stephen O'Connor, Walnut Creek, CA (US); Conor Joseph Heneghan, Campbell, CA (US); Xi Zhang, San Francisco, CA (US); Hamed Vavadi, Fremont, CA (US); Chris Hanrahan Sarantos, San Francisco, CA (US); Peter Colin Dess, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 0 days.

(21) Appl. No.: 16/439,467

(22) Filed: Jun. 12, 2019

(51) Int. Cl.
*A61B 5/1455* (2006.01)
*A61B 5/0205* (2006.01)
(Continued)

(52) U.S. Cl.
CPC .......... *A61B 5/0205* (2013.01); *A61B 5/0002* (2013.01); *A61B 5/14532* (2013.01);
(Continued)

(58) Field of Classification Search
CPC . A61B 5/0205; A61B 5/1455; A61B 5/14551; A61B 5/14552; A61B 5/14535;
(Continued)

(56) References Cited

U.S. PATENT DOCUMENTS 5,524,617 A * 6/1996 Mannheimer ...... A61B 5/14551
356/41
5,964,701 A * 10/1999 Asada ................ A61B 5/02438
600/300
(Continued)

FOREIGN PATENT DOCUMENTS

| CA | 2931973 | 6/2015 |
| CN | 106104408 | 11/2016 |

(Continued)

OTHER PUBLICATIONS

U.S. Appl. No. 62/006,835, filed Jun. 2, 2014 for "Wearable Computing Device" in the name of Motiv, Inc.
(Continued)

*Primary Examiner* — Chu Chuan Liu
(74) *Attorney, Agent, or Firm* — Hogan Lovells US LLP (57) ABSTRACT

Disclosed herein is a ring-shaped wearable device for detecting biometrics with a light source and a photodetector directed towards a digit wearing the ring-shaped device. The ring can thus detect oxygen saturation of a wearer based on light transmitted through the wearer's finger. The ring can include power saving measures to extend the battery life. A motion sensor can help determine opportune moments for data collection such as when the wearer is still. The motion sensor can be used to remove noise from the data caused by motion. After data is collected or during data collection, the ring can wirelessly communicate the data to another portable electronic device such as a phone or watch.

20 Claims, 8 Drawing Sheets

(51) Int. Cl.
*A61B 5/00* (2006.01)
*A61B 5/145* (2006.01)
*G01N 33/49* (2006.01)
*G01N 21/3577* (2014.01)
*A61B 5/024* (2006.01)
*A61B 5/021* (2006.01)

(52) U.S. Cl.
CPC ...... *A61B 5/14535* (2013.01); *A61B 5/14546* (2013.01); *A61B 5/14552* (2013.01); *A61B 5/6826* (2013.01); *G01N 21/3577* (2013.01); *G01N 33/4925* (2013.01); *A61B 5/021* (2013.01); *A61B 5/02438* (2013.01); *A61B 2562/0219* (2013.01)

(58) Field of Classification Search
CPC . A61B 5/14532; A61B 5/6826; A61B 5/0002; A61B 5/14546; A61B 5/021
See application file for complete search history.

(56) References Cited

U.S. PATENT DOCUMENTS

| | | | |
|---|---|---|---|
| 6,402,690 B1 * | 6/2002 | Rhee | A61B 5/0002 600/300 |
| 6,879,850 B2 * | 4/2005 | Kimball | A61B 5/14551 600/336 |
| 8,554,297 B2 * | 10/2013 | Moon | A61B 5/746 600/323 |
| D756,999 S | 5/2016 | von Badinski et al. | |
| 9,582,034 B2 | 2/2017 | von Badinski et al. | |
| D791,764 S | 7/2017 | von Badinski et al. | |
| D791,765 S | 7/2017 | von Badinski et al. | |
| D804,471 S | 12/2017 | von Badinski et al. | |
| D809,782 S | 2/2018 | von Badinski et al. | |
| D810,016 S | 2/2018 | von Badinski et al. | |
| D817,496 S | 5/2018 | Stirn et al. | |
| 9,958,904 B2 | 5/2018 | von Badinski et al. | |
| D828,767 S | 9/2018 | von Badinski et al. | |
| 10,126,779 B2 | 11/2018 | von Badinski et al. | |
| 10,139,859 B2 | 11/2018 | von Badinski et al. | |
| 10,156,867 B2 | 12/2018 | von Badinski et al. | |
| 10,281,953 B2 | 5/2019 | von Badinski et al. | |
| 10,331,168 B2 | 6/2019 | von Badinski et al. | |
| 2006/0122520 A1 * | 6/2006 | Banet | A61B 5/021 600/503 |
| 2015/0201875 A1 * | 7/2015 | Tateda | A61B 5/6826 600/324 |
| 2017/0119266 A1 * | 5/2017 | Wong | A61B 5/14552 |
| 2018/0042513 A1 * | 2/2018 | Connor | A61B 5/1455 |
| 2019/0086951 A1 | 3/2019 | von Badinski et al. | |
| 2019/0204865 A1 | 7/2019 | Von Badinski et al. | |
| 2019/0384354 A1 | 12/2019 | von Badinski | |
| 2020/0089272 A1 | 3/2020 | von Badinski | |

FOREIGN PATENT DOCUMENTS

| | | |
|---|---|---|
| EP | 3074838 | 8/2017 |
| JP | 2017-506376 | 3/2017 |
| WO | 2015/081321 | 6/2015 |

OTHER PUBLICATIONS

U.S. Appl. No. 61/910,201, filed Nov. 29, 2013 for "Finger Ring Device for Activity Monitoring or Gestural Input" in the name of Motiv, Inc.

* cited by examiner

RING FOR OPTICALLY MEASURING BIOMETRIC DATA

BACKGROUND

Recent advances in technology, including those available through consumer devices, have provided for corresponding advances in health detection and monitoring. For example, devices such as fitness bands and smart watches are able to determine information relating to the health of a person wearing the device. One use of these devices is to detect pulse oximetry. Pulse oximetry is a noninvasive method for monitoring a person's oxygen saturation and can be useful in monitoring a variety of health conditions. Traditional devices for monitoring oxygen saturation which are found in hospitals are typically tethered and are generally uncomfortable and unsuitable for normal wear. Smart watches and other "smart" devices that have attempted to measure oxygen saturation are generally less reliable and have limited battery life.

BRIEF DESCRIPTION OF THE DRAWINGS

Various embodiments in accordance with the present disclosure will be described with reference to the drawings, in which.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Approaches in accordance with various embodiments provide for the measurement of biometrics using a ring placed on a digit, such as a user's finger. The ring can comprise a compact housing including light source(s) for sending light through, or towards, the finger and photodetector(s) for detecting the light that is reflected from and/or transmitted through at least a portion of the finger. The combination of the light source(s) and the photodetector(s) can be used to detect absorption of light at, for example, one wavelength in comparison to light at another wavelength. The different rates of absorption can be used to calculate biometric data, such as the oxygen saturation. Such a ring-shaped device can monitor other biometric information as well, and can transmit the biometric information to another device for further analysis, display, or other such usage.

Various other functions can be implemented within the various embodiments as well as discussed and suggested elsewhere herein.

Many portable electronic devices such as smart watches include functionality for measuring various biometric information. For example, many include capability for measuring oxygen saturation using reflective techniques. For example, an LED and a photodetector might be on an inward facing side of a smart watch. The LED can illuminate a user's skin and the photodetector can detect light that reflects back towards the watch. This approach however suffers significant drawbacks. One problem is that an interior surface of a watch does not always rest flush against the skin of the wearer. While reflective detection might generally provide more noisy data in comparison to transmissive detection, the noise can be exacerbated when there is not contact with the skin and the exterior surface of the skin reflects light towards the photodetector 202. Another problem with traditional smart devices is that they have limited battery life. Because they include display screens and other functionality outside of biometric monitoring, their battery life is limited to typically less than a day. A limited battery life makes all-day monitoring impossible. For example, if a user wears their smart watch during the day, they will likely recharge their watch at night. This is problematic for users who wish to monitor their oxygen saturation throughout the day and night.

Dedicated oxygen saturation measurement devices are traditionally unsuited for casual every-day type of wear. For example, they are typically clamped onto the tip of the finger thus preventing the user from performing typical daily operations such as grabbing items, typing, etc. Further, these devices are typically tethered to an external power source or external processing equipment which severely limits the mobility of the user.

The present solution enables users to wear a biometric device in such a way to accommodate their lifestyle. Disclosed herein is a ring with a light source and a photodetector directed inwards on a ring. The ring can thus detect oxygen saturation of a wearer based on light transmitted through the wearer's finger. The ring can include power saving measures to extend the battery life. A motion sensor can help determine opportune moments for data collection such as when the wearer is still. The motion sensor can be used to remove noise from the data caused by motion. After data is collected or during data collection, the ring can wirelessly communicate the data to another portable electronic device such as a phone or watch. In some embodiments, the data can be communicated over near field communications (NFC) protocol while the user is holding their phone and the ring is in close proximity to the phone.

Figure 1:
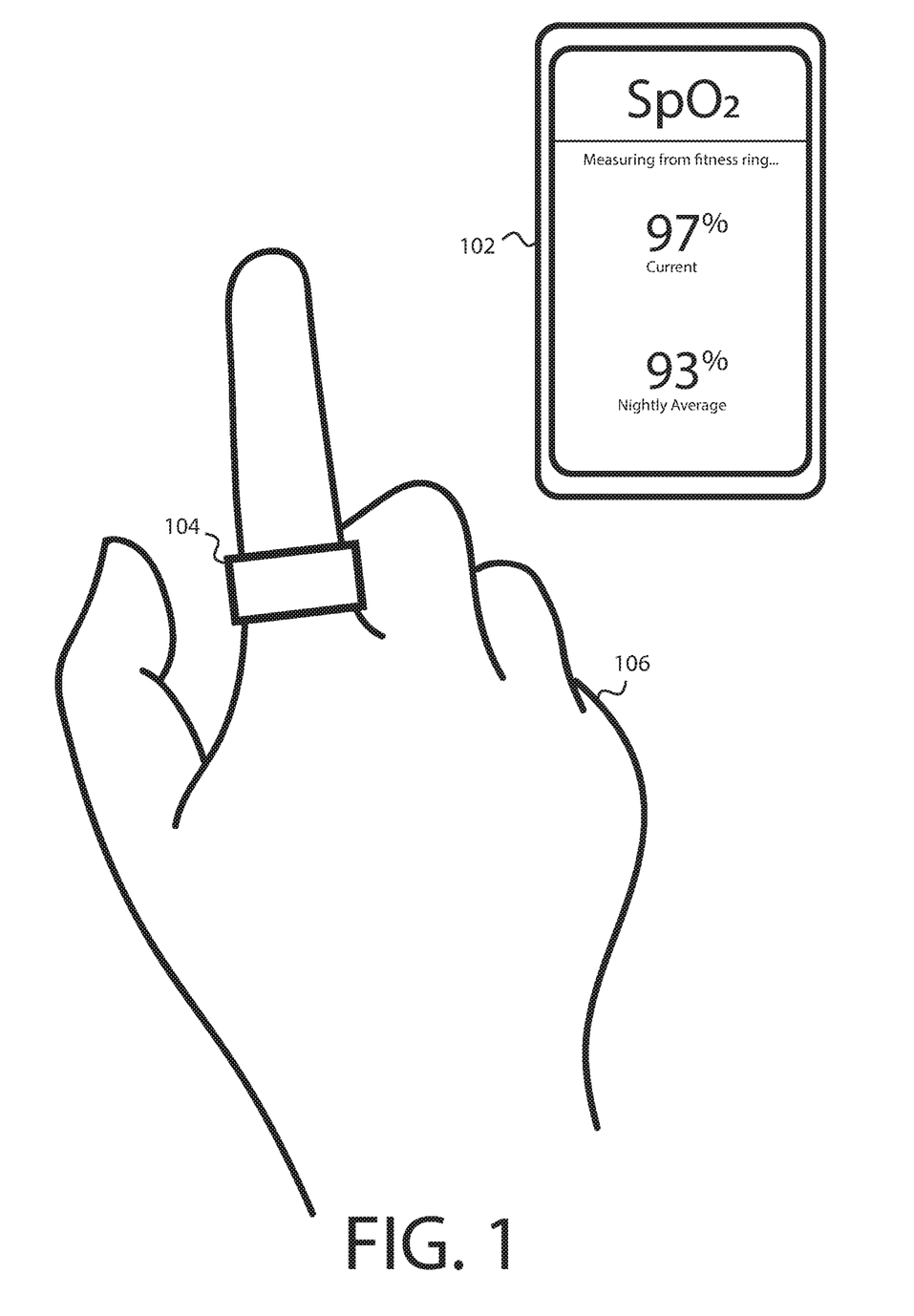
FIG. 1 illustrates an example ring according to various embodiments.

FIG. 1 illustrates an example ring 104 according to various embodiments. For example, a user can wear a ring 104 on a finger of the user's hand 106. The user can then connect to the ring 104 with a portable electronic device 102 such as a phone or watch. The ring 104 can collect biometric data and periodically send the data to the portable electronic device 102 for processing, display, and/or retransmission to a networked service. The ring 104 can implement power saving measures to prolong the battery life. The ring 104 can generally be in a low power state unless it is measuring data or transmitting data to another device, thus extending the battery life in comparison to traditional approaches. The battery life can be a few days to a number of weeks depending on use.

The ring 104 can be worn on a wearer's finger. The ring 104 can be worn between two knuckles of the finger. This can leave the tip of the finger unobstructed for common tasks. The thickness of the band can be minimized to accommodate free movement of the finger in relation to other fingers. In some embodiments, a larger ring can be designed which fits over the thumb of a wearer. In some embodiments, a combination of multiple rings can be utilized wherein each ring has different functionality. The multiple rings can be worn on the same finger in a stacked form or can be worn on separate fingers. In some embodiments, one ring can be worn on a first finger and a second ring can be worn on another finger. A two-fingered setup can include a flexible or rigid connection between the rings. If multiple rings are used, they can be in electronic communication through electric contacts that physically can touch or wireless communication using a wireless protocol. In some embodiments, the "ring 104" can be wider than a traditional ring 104 and can be a flexible sleeve worn on a user's finger. For example, the ring 104 can be like the finger of a glove. In some embodiments, features of the ring 104 can be added to a traditional ring 104. For example, a light source 204, photodetector 202, and other elements can snap onto a traditional ring 104. The ring 104 can have an opening that is elliptical or any other shape through which a digit can pass. In some embodiments, the device can envelop a digit, taking the form of a thimble, glove, etc.

It should be understood that the principles herein disclosed in relation to a ring 104 can be applied to rings 104 worn on other places aside from the finger as well as other systems. For example, an earring can be worn on a user's earlobe and can shine a light through the lobe for detection on the other side of the ear. The principles can also apply to a navel ring 104, nose ring 104, anklet, bracelet, device placed over the tip of a finger such as a soft thimble, etc. In some embodiments, the principles herein disclosed can be applied to a glove (e.g., a photodetector 202 can be on one side of the glove and a light source 204 can be on the other side; light can then be passed through the palm of the gloved hand). Similarly, the principles herein can be applied to a shoe or sock whereby a light source 204 can shine light through a toe or arch of a person's foot.

A user's portable electronic device 102 can periodically receive data from the ring 104 over a wireless communications protocol. The portable electronic device 102 can be a phone, smart watch, fitness tracker, etc. The portable electronic device 102 can receive data from the ring 104 once a second, minute, day, etc. In some embodiments the portable electronic device 102 polls the ring 104 to determine if there is new data to receive; additionally or alternatively the ring 104 can push new information to the portable electronic device 102 as it become available and/or according to a power policy. In some embodiments, the ring 104 can transmit data to a less portable electronic device such as a desktop computer or networked computer. For example, the ring 104 can send data to the portable electronic device 102 using a low power wireless protocol and the portable electronic device 102 can send the information to a networked server using a higher power wireless protocol (e.g., WiFi or cellular network).

The user experience can generally be seamless as the ring 104 can have an extended battery life and can automatically transmit data to a portable electronic device 102 that the user already owns and uses. Further, the ring 104 can provide more accurate biometric information that a smart watch or similar device because the ring 104 abuts the users skin more completely and reliably.

FIGS. 2A-2E illustrate example configurations of a ring 104 according to various embodiments. The ring 104 can include a light source 204 and a photodetector 202. For the purposes of these illustrations, the photodetector 202 is illustrated using an empty rectangle whereas the light source 204 104 is illustrated using a rectangle with a dark rectangle inside. FIG. 1 illustrates how a single light source 204 can be located separately from a single photodetector 202.

A system can utilize the ring 104 to monitor the oxygen saturation (SpO2), pulse, blood pressure, glucose levels, lipid concentration, carboxyhemoglobin levels, hemoglobin concentration (hematocrit levels), etc. In some embodiments, the ring 104 can monitor pulsatile (arterial) blood oxygenation ("SpO2") or non-pulsatile (arterial and venous blood, usually called tissue oxygenation or "StO2"). These measurements can largely be taken by measuring the transmission and/or reflection of light through a user's finger. For example the light source 204 can emit light through the finger of a user which can be partially absorbed by the finger and then detected at the photodetector 202. Based on which wavelengths of light are absorbed by the finger, the system can determine the oxygen saturation in the user's body.

Oxygenated hemoglobin (HbO2) absorbs red light and infrared light differently than deoxygenated hemoglobin (Hb). For example, HbO2 absorbs less red light than Hb while at higher wavelengths of light, HbO2 absorbs more light than Hb. By comparing the absorption of red to infrared light, a system can determine the SpO2 in the user's body. Measurements taken over time can help overcome noise in the data. For example, the system can identify a pulse in the data and use that as a baseline to compare for oxygen saturation calculations.

The ring 104 can utilize a light source 204 such as a light emitting diode (LED), a laser diode, filtered broadband light source, etc. A light source 204 can be used which emits a certain primary wavelength of light (e.g., infrared or red light). A light source 204 can be used which emits light according to a wide range of wavelengths (e.g., "white" light that mimics natural sunlight). In some embodiments, one or more filters can be placed on a light source 204 to limit the wavelengths of transmission. In some embodiments, multiple light sources 204 can be independently activated. For example, a red LED can be activated and then an infrared LED can subsequently be activated. In some embodiments, light guides can provide the light from a single light source 204 to various locations of the ring 104. In some embodiments, ambient light is utilized as the light source 204. For example, the ring 104 can detect ambient light that passes at least partially through a finger of the user. Other external light sources 204 are contemplated.

The ring 104 can utilize a photodetector 202 such as a photodiode and/or phototransistor to detect the amount of light that passes through a finger of a user from the light source 204. The photodetector 202 can detect light reflected within the finger and/or transmitted through the finger. A photodetector 202 can be configured for a particular wavelength of light such as red or infrared light. For example, a photodetector 202 can have a filter configured to permit the particular wavelength of light to pass. In some embodiments, the photodetector 202 is not configured for a single wavelength of light but can be activated by multiple wavelengths of light. Such a configuration can be useful when multiple light sources 204 are used with corresponding wavelengths (e.g., a red light source 204 can be activated followed by an infrared light source 204).

Figure 2A:
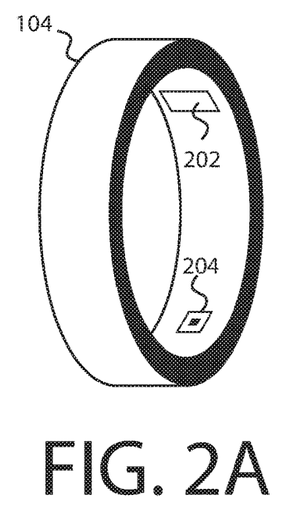
FIGS. 2A-2E illustrates example light source and photodetector configurations according to various embodiments.

In some embodiments, the light source 204 is positioned largely opposite of the photodetector 202 as shown in FIG. 2A. This can facilitate transmissive readings of light that passes through the finger. In some embodiments, the light source 204 is positioned closer to the photodetector 202. For example, the light source 204 can be positioned next to the photodetector 202. This can facilitate reflective readings of the light that reflects off the interior of the finger. The placement of the light source 204 relative to the photodetector 202 can be varied to obtain a blend of transmissive and reflective readings. For example, if the photodetector 202 is placed at a 90 degree offset from the light source 204 (e.g., a quarter of the way around the ring 104), then a portion of the light that the photodetector 202 receives will be transmissive, passing directly from the light source 204 to the photodetector 202, whereas a portion will be reflective, bouncing off the inside of the finger and arriving at the photodetector 202. Other offsets are contemplated; for example, the photodetector 202 can be placed 10 degrees, 15 degrees, 30 degrees, 45 degrees, 110 degrees, etc. from the light source 204 (e.g., around the ring 104).

It should be understood that there can be multiple photodetectors 202 and multiple light sources 204. Furthermore, it should be understood that a single photodetector 202 can be used to take readings from various light sources 204 and a single light source 204 can provide light to multiple photodetectors 202. For example, if a ring 104 includes a photodetector 202 at its "top" (e.g., 0 degrees), it can include light sources 204 at 0 degrees, 45 degrees, 90 degrees, etc. around the ring 104. These light sources 204 can be separately activated and read by the photodetector 202. For example, the light source 204 at 0 degrees can be activated and recorded by the photodetector 202; the light source 204 at 45 degrees can then be activated and detected by the photodetector 202, followed by the light source 204 at 90 degrees, and so on. Similarly, a single light source 204 (e.g., at 0 degrees) can emit light for detection at multiple photodetectors 202 around the ring 104 (e.g., at 0 degrees, 45 degrees, 90 degrees, etc.). Thus, multiple light sources 204 can be detected by multiple photodetectors 202, in combination (e.g., multiple light sources 204 detected by a single photodetector 202 and/or a single light source 204 detected by multiple photodetectors 202) and/or in alternating groupings of light sources 204 and photodetectors 202. By emitting and detecting light in various combinations, the system can help minimize noise in the data (e.g., from ambient light). Thus, multiple photodetectors can detect respective light paths from a single source, a single photodetector can detect multiple light paths from multiple light sources, etc.

Figure 2B:
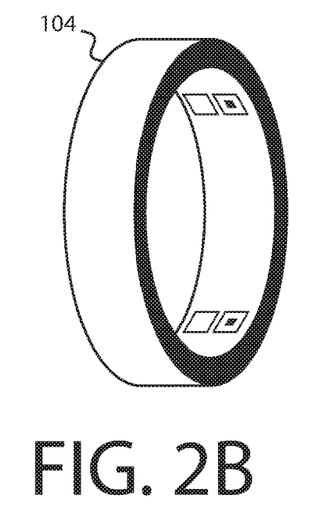

In FIG. 2B, a first location on the ring 104 can include a light source 204 and photodetector 202 and a second location on the ring 104 can include another light source 204 and photodetector 202. The ring 104 can take a measurement using the top light source 204 and the bottom photodetector 202. The ring 104 can then take measurements using various combinations of the light sources 204 and photodetectors 202. Combinations can include the bottom light source 204 and the top photodetector 202, the top light source 204 and top photodetector 202, the bottom light source 204 and bottom photodetector 202, the top and bottom light sources 204 and the bottom photodetector 202, the top and bottom light sources 204 and the top photodetector 202, the top and bottom photodetectors 202 and the top light source 204, the top and bottom photodetectors 202 and the bottom light source 204, and so on. Each combination can be activated for a period comprising a few milliseconds to a few seconds. For example, each combination can be activated multiple times during a single heartbeat. In some embodiments, each combination is activated during a single heartbeat or multiple heartbeats before a second combination is activated. In some embodiments, different combinations are configured for certain wavelengths of light that are slightly different, thus allowing the different combinations to be active simultaneously.

In some embodiments, only a subset of light sources 204 and photodetectors 202 might have adequate contact with the skin of the user to provide reliable measurements. The system can analyze the data for various combinations and determine which photodetector 202(s) and/or light source 204(s) have adequate contact with the skin. For example, the system can identify measurements that have sudden changes (e.g., indicating skin coming into and out of contact with the skin), low variance (e.g., indicating that the light coming in might be ambient light or light passing around the finger and not through the finger), etc. When reliable light source 204(s) and/or photodetector 202(s) are determined, unreliable light source 204(s) and photodetector 202(s) can be deactivated. This can help preserve power and limit the amount of unreliable data being collected.

Figure 2C:
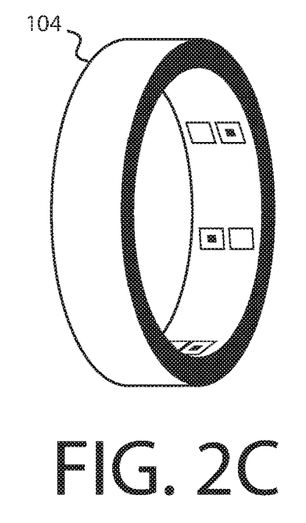

FIG. 2C illustrates how light sources 204 and photodetectors 202 can alternate locations as they are placed around the ring 104. For example, one light source 204 can be placed closer to the fingertip while another light source 204 can be place further from the fingertip. This can enable various photodetector 202 and light source 204 combinations that have different light paths through the finger. For example, one light path might be largely obstructed by bone or fat whereas a light path close to the fingertip is less obstructed. Various combinations of photodetectors 202 and light sources 204 can be activated in sequence to determine an optimal light path or otherwise enhance the quality of received data.

Figure 2D:
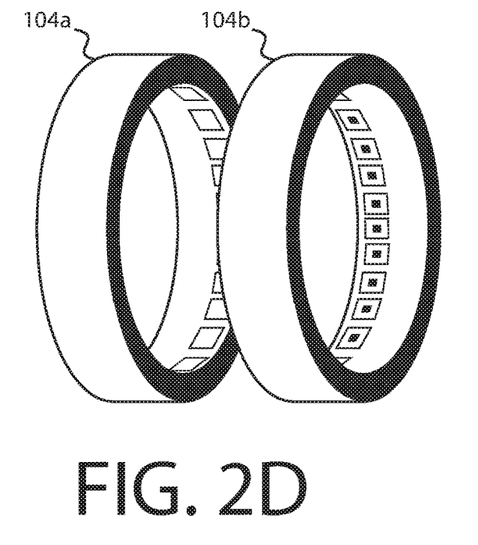

The photodetector 202 can be offset from the light source 204 along an axis of the ring 104. For example, if the ring 104 is wide enough, the light source 204 can be positioned closer to the fingertip (while the ring 104 is worn) while the photodetector 202 can be positioned further from the fingertip. In some embodiments, multiple rings 104 can be designed to be worn together. As shown in FIG. 2D, in some such embodiments, one ring 104b can include a light source 204 while another ring 104a can include a photodetector 202. This can increase the offset between the light source 204 can photodetector 202 which can be beneficial in obtaining a reading in some embodiments.

In some embodiments, a first ring 104b can include somewhat standardized light sources 204 and additional ring(s) 104a can include various photodetector(s) 202 or other sensors for various purposes. For example, a user can purchase a photodetector 202 ring 104 that is more sensitive at a higher cost than a photodetector 202 ring 104 that is less sensitive. Multiple photodetector 202 rings 104 can be stacked on a finger for different purposes.

Figure 2E:
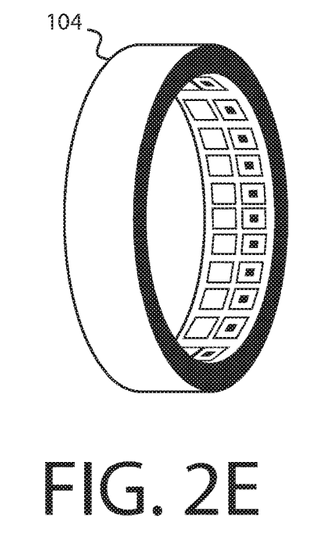

FIG. 2E illustrates how a ring 104 can include photodetectors 202 and/or light sources 204 that continue around the interior of the ring 104. In some embodiments, the photodetectors 202 and light sources 204 can be independently addressed such that the ring 104 can activate various combinations of photodetectors 202 and light sources 204. These combinations can be activated sequentially to provide a more complete sampling of the oxygen saturation of the user. For example, if there are twenty photodetectors 202 and twenty light sources 204 around the interior of the ring, a first photodetector 202 can be activated with an opposing light source 204 (e.g., on the opposite side of the ring) followed by a second photodetector 202 light source 204 combination, until all twenty opposing combinations are activated. In some embodiments, a light guide can enable light from a single light source to emit light at different parts of the ring 104. Similarly, a light guide can direct light from different parts of the ring 104 to a single photodetector 202.

Figure 3:
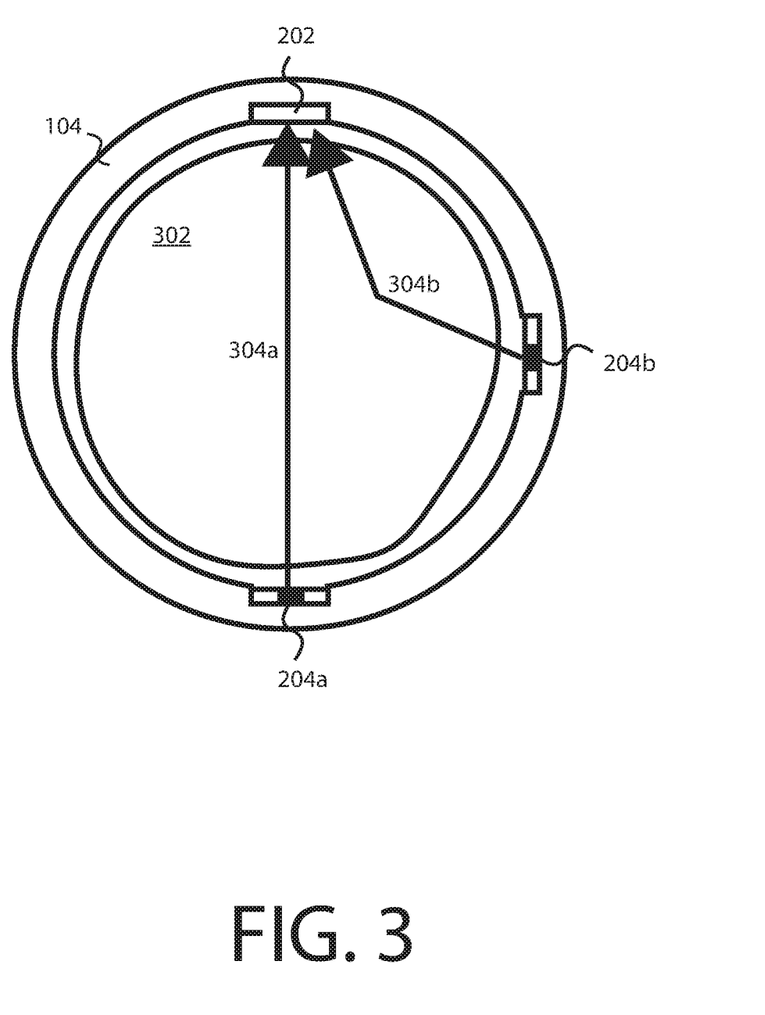
FIG. 3 illustrates an example cross section of the ring and finger according to various embodiments.

FIG. 3 illustrates an example cross section of the ring 104 and finger 302. A photodetector 202 can be placed on one part of the ring 104 while two light sources 204a and 204b can be placed on other parts of the ring 104. The combination of the light source 204a and photodetector 202 can be used to capture absorption of the finger 204 along light path 304a. The combination of light source 204b and photodetector 202 can be used to capture absorption of the finger 204 along light path 304b. The system can compare the absorption detected for light paths 304a and 304b and determine which light path 304 provides more accurate information. For example, light path 304a might be occluded by a bone inside the finger 302 or light path 304b might have interference from light that travels through the surface of the skin or reflects between the skin and ring 104.

FIG. 3 also illustrates how one light path 304a can largely be a transmissive light path 304 that passes through the finger whereas another light path 304b can be more reflective, relying on the reflection of the light within the finger. Because transmissive light paths 304 largely measure the absorption of the body and reflective light paths 304 largely measure the reflection of the body, a system can adjust the data accordingly. Data received can be tagged as transmissive data, reflective data, or a combination thereof. A system processing the data can incorporate this information.

Figure 4A:
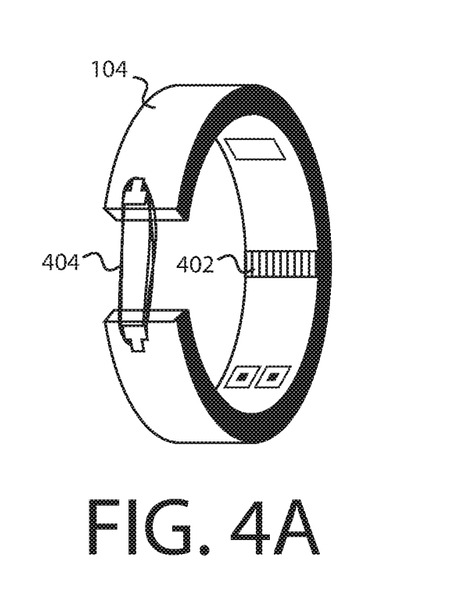
FIGS. 4A-4D illustrates example light techniques for controlling light according to various embodiments.

FIGS. 4A-4D illustrate example light techniques for controlling light according to various embodiments. In FIG. 4A, the ring 104 is constructed with a hinge 402 and connection 404 whereby the ring can be tightened to a comfortable fit around the finger. Having a tight and comfortable fit allows the photodetector 202 and light source 204 to have better contact with the skin of the finger. The ring 104 in FIG. 4A can be adjustable. In some embodiments, the ring 104 is flexible and adjustable in size. In some embodiments, the connection 404 is an elastic element that pulls the two halves of the ring 104 together. Other clasping mechanisms are contemplated.

Figure 4B:
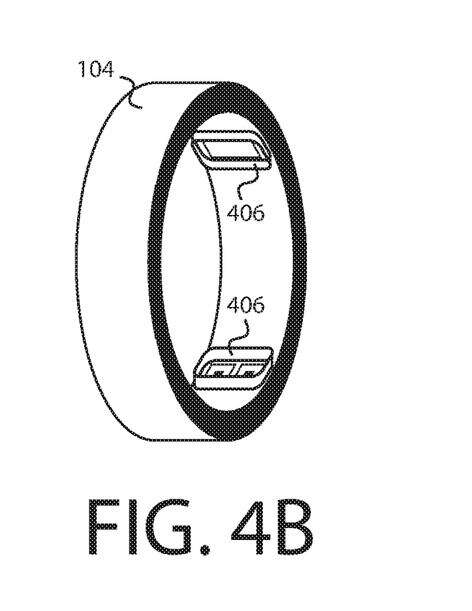
Figure 4C:
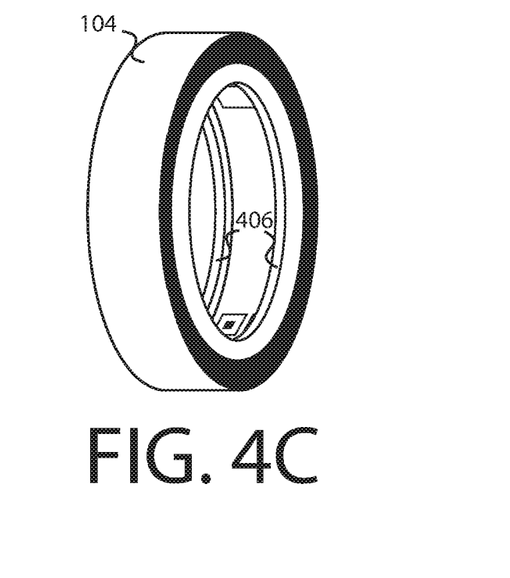
Figure 4D:
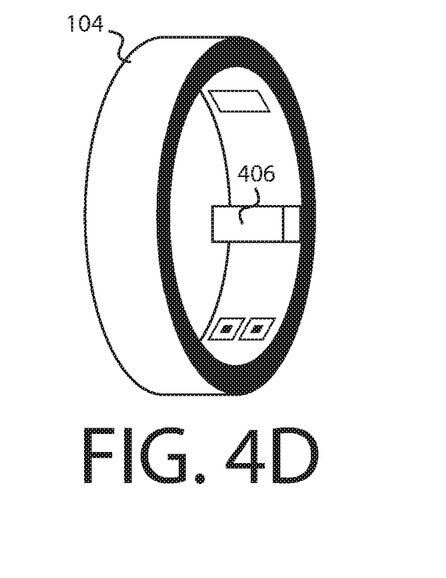

In FIGS. 4B-4D, opaque light barriers 406 are shown on the ring 104 to minimize the amount of unwanted light by the photodetector 202. For example, an opaque barrier 406 can encircle the photodetector 202 and can ensure that only light from the finger is received by the photodetector 202 and ambient light is blocked out as shown in FIG. 4B. The opaque light barrier(s) 406 can be flexible so that they can form to the surface of the finger can create a close fit and prevent light leakage. An opaque barrier 406 can similarly encircle the light source 204 to block light that is not passed through the user's finger. As shown in FIG. 4C, in some embodiments, such an opaque barrier 406 can be placed around the ring 104 on both sides (e.g., towards the fingertip and the side away from the fingertip) to create a tight seam between the ring 104 and the finger wherein little ambient light might interfere with readings of the photodetector 202. As shown in FIG. 4D, the opaque barrier 406 can be placed on the ring 104 in between the photodetector 202 and the light source 204 to prevent light leakage along the surfaces of the finger and ring.

The ring 104 can include elements to direct light from the light source 204, through the finger, to the photodetector 202. For example, the ring 104 can include a reflective material on parts of the ring's 104 interior to reflect some light back through the finger towards the photodetector 202. This reflective material can be placed near the light source 204. The ring 104 can include a dark material that absorbs light to minimize reflections around the surface of the finger. In some embodiments, the ring 104 includes a lens on or near the light source 204 and/or the photodetector 202 to better guide light paths through the finger.

The ring 104 can be rigid, flexible, or a combination of rigid and flexible. For example, the ring 104 can have a rigid area holding a printed circuit board with a flexible band completing the ring 104. The flexible band can contain one or more photodetectors 202 and light sources 204. The ring 104 can thus have a design similar to a miniature watch, but with functionality within the band. In some embodiments, components described herein can be affixed to standard or traditional rings 104.

Figure 5:
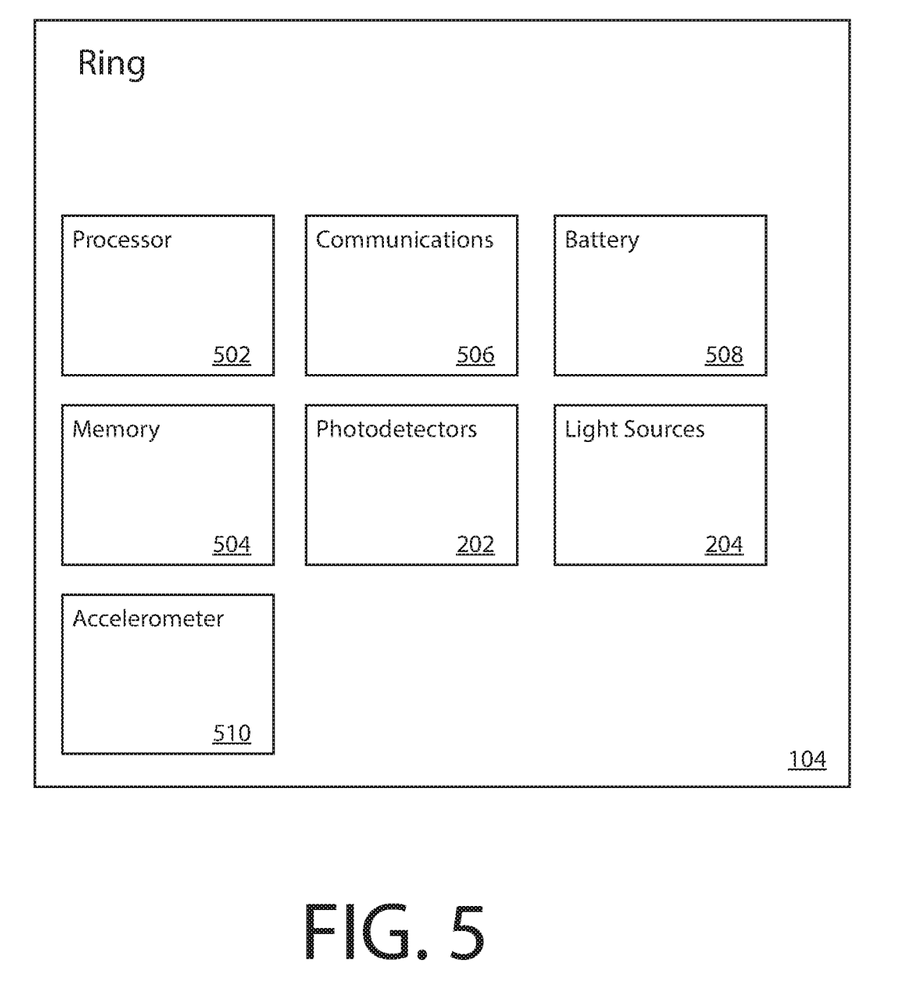
FIG. 5 illustrates an example organizational diagram for example components within a ring according to various embodiments.

FIG. 5 illustrates an example organizational diagram for example components within a ring 104. The ring 104 can include a processor 502 for analyzing data and preprocessing data before transmitting it to a portable electronic device. The processor 502 an also maintain and utilize security credentials for connecting to various networks and services. The ring 104 can include memory such as flash memory for storing data. The ring 104 can include communications circuitry for wireless and/or wired communications. For example, the ring 104 can use cellular networking, WiFi (e.g., 802.11x), Bluetooth, or other wireless protocols for communicating information to a smart watch, fitness band, cell phone, or other device. In some embodiments, the ring 104 can communicate to a user's phone using near field communication (NFC) while the user holds the phone. In some embodiments, the ring 104 can communicate to a smart watch which can relay information to a phone. For example, the ring 104 can communicate to a smart watch or fitness tracker using an ultra-low power wireless protocol and the smart watch/fitness tracker can then communicate the information to the user's phone using Bluetooth.

The ring 104 can include a battery or some other energy storage mechanism. In some embodiments, the ring 104 can store kinematic energy using a spring. In some embodiments, the battery is a capacitor that holds enough charge to operate the ring 104 for an extended period of time. The ring 104 can have an internal power source. For example, the ring 104 can have a battery and/or capacitor to hold energy. The ring 104 can be recharged periodically. For example, the user can place the ring 104 on an inductive charging stand. The ring 104 can have electrical contacts for receiving a charge. The ring 104 can receive energy from a nearby smart device such as a smart watch. This power can be communicated wirelessly. In some embodiments, a user's phone can be used to charge the device. For example, while a user holds their phone, it can be in close proximity to the ring 104 and can wirelessly charge the ring 104. In some embodiments, the ring 104 can have a kinetic energy storage mechanism. For example, as the user moves their hand, a weight and spring can be used to store energy.

The ring 104 can have environmental sensors such as accelerometers 510, barometers, magnetometers, gyroscopes, etc. The system can identify when the user is relatively still using these environmental sensors. This can help minimize the amount of data that is unusable because of noise caused by movement. In some embodiments, data from the environmental sensors can help adjust data from the photodetector(s) to account for motion. For example, if the system is measuring the pulse of the user, it can determine that variations of the data are largely caused by movement.

The ring 104 can present information to a user. For example, the ring 104 can include a display or LEDs directed outwards to indicate a status of the ring 104. Such an LED can indicate a battery level for the ring 104. A display can show the most recent oxygen saturation readings. The ring 104 can indicate wireless connectivity or lack thereof. The ring 104 can indicate if the user is overdue for a reading. This might occur if the user has been active and the user's finger has not been idle long enough for the ring 104 to obtain an accurate measurement. The ring 104 can indicate that it has new data for download to a portable electronic device and/or other system. This can help the user know that they need to connect the ring 104 or otherwise facilitate the download of information. In some embodiments, other feedback mechanisms can indicate a status of the ring. Such feedback mechanisms can supply gentle heat or electric pulse to the user or vibrational feedback.

A system can use this information to provide certain health data to a user and/or healthcare professional. For example, a user suffering from a sleep disorder such as sleep apnea can use the ring 104 to monitor their oxygen saturation throughout the evening. A system can use this data to detect menstrual patterns in a user, eating habits of the user, hydration of the user, and other vital signs of a user. The system can then present the user with a visual indication of this information. If the system detects an anomaly, it can alert the user or care provider.

The system can analyze data from the photodetectors to determine or predict various health parameters for the user or other interested an authorized parties. The user can see live data as to the user's current heart rate and oxygen saturation. If live data is not available (e.g., if the ring 104 only acquires or transmits data on a periodic basis) then the system can periodically display updates of the user's health information. In some embodiments, the system can provide feedback to the user about the user's health status. For example, the system can indicate that the user might not have slept well because of the user's SpO2 levels over the night. Because hemoglobin saturation and heart rate might change based on a woman's menstrual cycle, the system can inform the user about an upcoming event in their cycle (e.g., ovulation, start of menstruation, etc.). The ring 104 can detect lipids and/or glucose concentration in the user's blood and can monitor the user's diet patterns. This can be helpful for those with dietary conditions that should be monitored like diabetics.

The biometric data can be used within a hospital environment. For example, a patient can wear the ring 104 which can be monitored by hospital staff. The ring 104 can communicate directly to a hospital network using, for example, WiFi. In some embodiments, the system can determine if some threshold is reached and can alert medical personnel. For example, if the heart rate, blood saturation, or glucose measurements are outside of an expected or healthy range.

Figure 6A:
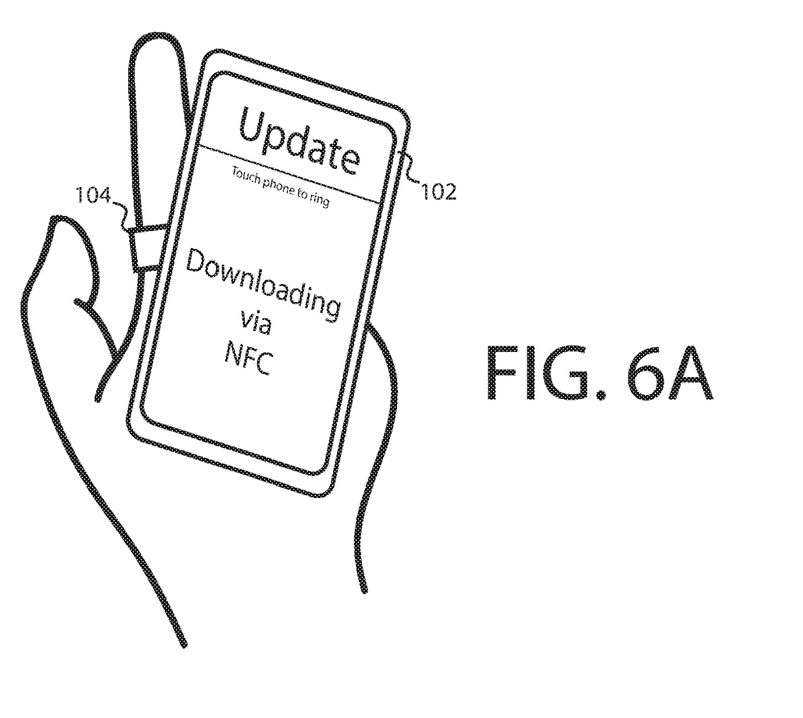
FIGS. 6A and 6B illustrate example techniques for retrieving data from the ring according to various embodiments.
Figure 6B:
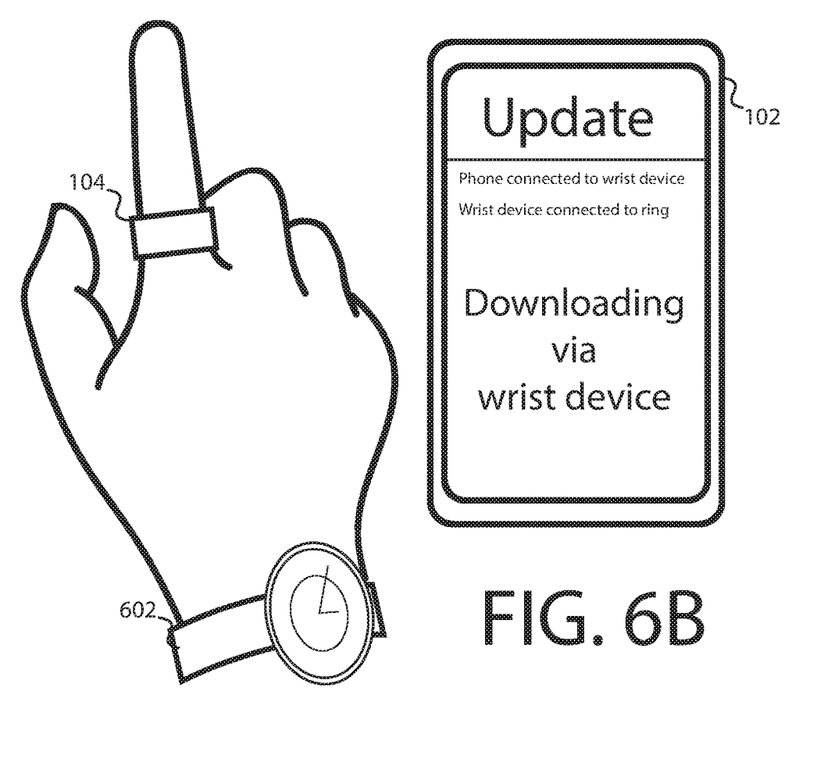

FIGS. 6A-6B illustrate example techniques for retrieving data from the ring 104 according to various embodiments. The ring 104 can be configured to communicate wirelessly to other devices. While some wireless protocols have extensive range, such protocols generally consume more energy than low-range protocols. The ring 104 can have a longer battery life by using lower power wireless protocols to communicate information. In FIG. 6A, the ring 104 can communicate to the portable electronic device 102 using near field communication (NFC). For example, the portable electronic device 102 can have an NFC antenna embedded in the back of the device and when it comes within proximity of the ring 104, the ring can begin transmitting data to the portable electronic device 102. In some embodiments, this NFC communication is powered completely by the portable electronic device 102 as would occur with "passive" NFC communications. For example, the portable electronic device 102 can charge a small capacitor in the ring 104 which can supply enough power to read data from a memory store on the ring 104 and transmit the data to the portable electronic device 102 using an NFC antenna. In some embodiments, the ring 104 is placed in a low power state until the portable electronic device 102 is within close proximity of the ring 104 based on the NFC connection. This technique can be useful because a natural position for holding the portable electronic device 102 might be such that the ring 104 is routinely located at an optimal position for NFC communication. Thus, downloads can happen without express user action. As the user uses their phone regularly, the phone can download information from the ring 102.

In FIG. 6B, a wrist device 602 can relay information from the ring 104 to the portable electronic device 102. For example, the ring 104 can communicate information to the wrist device 602 over a first wireless protocol and the wrist device 602 can communicate the information to the portable electronic device 102 over a second wireless protocol. The two communications can be over the same wireless protocol but at different power levels. The wrist device 602 can be a smart watch, fitness tracker, or other device.

In some embodiments, raw data is transmitted from the ring 104. This raw data can be processed at the wrist device 602 and/or the portable electronic device 102. The processing can include filtering unreliable data or outlying data. The processing can include determining a pulse of the user, an oxygen saturation of the user, etc. In some embodiments, the ring 104 performs preprocessing of the data. Further processing can determine the health status of a user such as determining that the user has a sleep apnea. In some embodiments, data can be sent to a networked service which can further analyze the data and generate reports for display on the users portable electronic device 102, ring 104, wrist device 602, etc.

Figure 7:
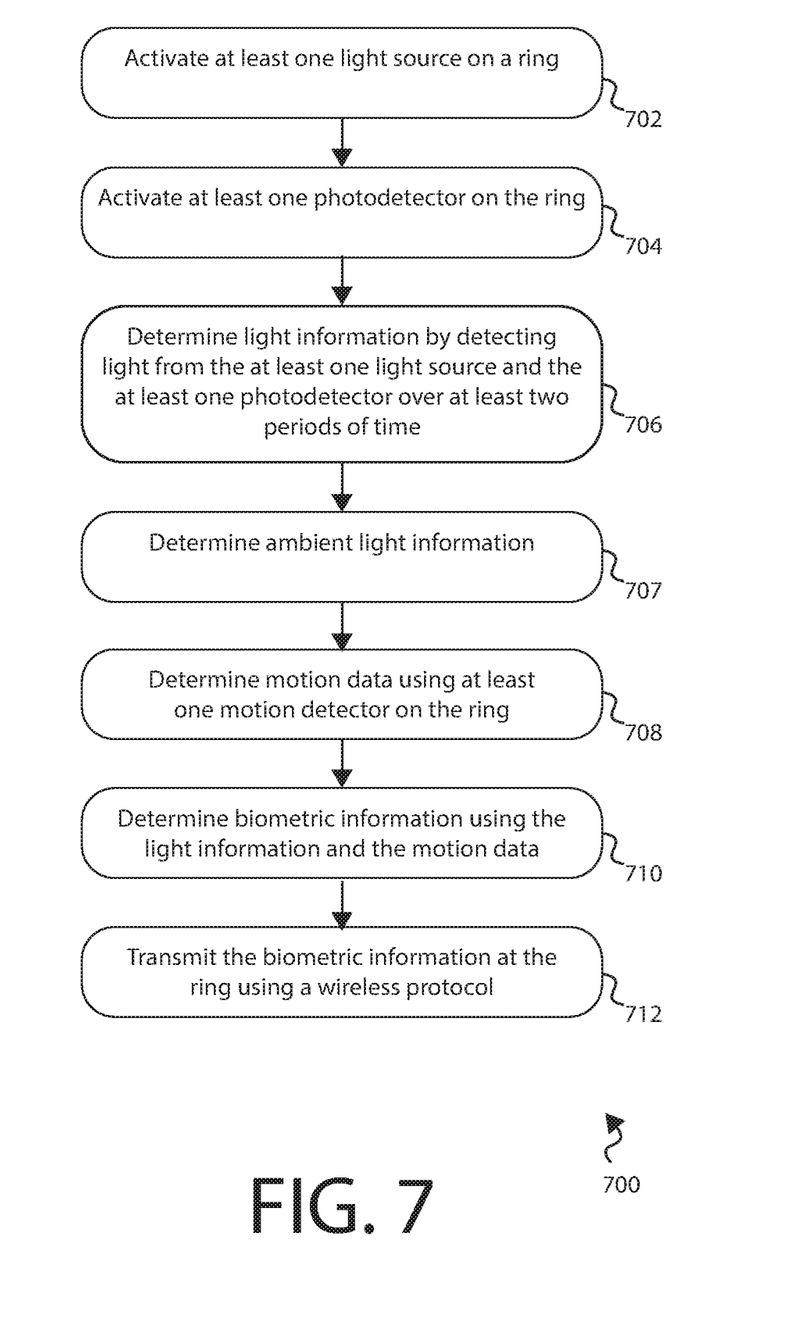
FIG. 7 illustrates an example method according to various embodiments.

FIG. 7 illustrates an example method 700 according to various embodiments. Measuring a person's blood oxygenation (SpO2) continuously in a form factor that they are willing to wear for long periods of time has been traditionally difficult. Continuous measurement overnight during sleep is needed to monitor for de-oxygenations related to sleep apnea. Traditional devices clip over the tip of the finger, or less commonly, attach to the ear or forehead. These traditional devices are uncomfortable, bulky, typically tethered, and otherwise unsuited for casual wear. These limitations hinder the functionality of the devices. Devices that are designed to be more user-friendly and/or comfortable typically make sacrifices in accuracy (e.g., by only using reflective observations).

The system can activate at least one light source on a ring 702. There can be multiple light sources on the ring. With multiple light sources, the light sources can be of the same type or different types. Each light source can be a light emitting diode (LED) or other light source. Various light sources can be configured to emit different wavelengths of light, whether inherently or through the application of filters. The LEDs can emit light with red wavelengths as well as infrared wavelengths. These two wavelengths can be used because they are effective at highlighting the differences between oxygenated and deoxygenated blood.

The system can activate at least one photodetector on the ring 704. There can be multiple photodetectors on the ring. The photodetector(s) can be configured for a single wavelength of light or a small band of wavelengths. In some embodiments, a photodetector can detect multiple wavelengths. A light filter can be placed on a photodetector to isolate certain wavelengths.

The system can determine light information by detecting light from the at least one light source and the at least one photodetector over at least two periods of time 706. For example, the light information can be measured at a first time period and a second time period. Thus the light information can include multiple readings corresponding to multiple time periods.

In some embodiments, there are multiple combinations of light sources and photodetectors which can be used to measure different light paths. For example, a first combination can include a first photodetector and a first light source and a second combination can include a second photodetector and a second light source. In some embodiments, the light source-photodetector combinations are reversed such that a first combination includes a photodetector positioned on the bottom of the ring and a second combination includes a photodetector positioned on the top of the ring. These different combinations can capture different light paths though the finger (or other body part) of a user. In some embodiments, a combination has multiple light sources combined with a single photodetector and/or multiple photodetectors combined with a single light source. In some embodiments, a light source is included in multiple combinations. In some embodiments, a photodetector is included in multiple combinations.

The system can take measurements using different combinations sequentially. For example, the system can take a measurement using a first combination and then take a measurement using the second combination followed by a measurement of the first combination again. A single combination might be occluded and not provide good measurements. Further, a single combination might have interference from ambient light because elements have an imperfect connection to the finger. The system can take measurements from multiple combinations throughout a measurement period. In some embodiments, the system can determine which combinations can provide optimal measurements and then only take measurements from those combinations during the measurement period.

A combination can include elements opposite of each other. For example, a photodetector on one side of the ring and a light source on the other side of the ring. This can enable transmissive measurements of light passing through the finger. In this design, red and infrared light sources can be incident on the palmar (ventral) side of the finger, just below the first knuckle (where a ring is worn), and a detector can receive the transmitted light on the opposite, dorsal side of the finger. Thus the optical path from light source to detector extends through the finger from the palm side to the back side. This can provide a more accurate reading in comparison to reflective readings. In some embodiments, the photodetector and light source can be positioned close to each other to facilitate reflective measurements. Other combinations are contemplated such as a 90 degree offset such that the light source is placed at the top of the finger and the photodetector is placed on the right side of the finger. Other configurations are contemplated.

In some embodiments, the ring device is configured like a sleeve over the finger. Such a sleeve can expose the fingertip. The ring device can be flexible and malleable. Flexibility of the device can be facilitated by using a flexible printed circuit board. In some embodiments, multiple rings can be used along an axis of the finger. One ring can include a light source and another ring can have a light detector. In some embodiments, different rings can separately gather data. The data from the separate rings can be compared to determine what data represents biometric information and which represent motion data or noise. The multiple rings can be on different fingers.

The system can gather data and analyze it to determine various characteristics of a user's finger. For example, the system can measure the blood oxygenation (e.g., SpO2) of a user, the heartbeat of a user, and other characteristics.

The advantage over existing blood oxygenation measuring and sleep monitoring equipment is that it allows a system to use a site on the body (the finger ring position) that is more comfortable. This makes apnea screening less burdensome to the user and is less likely to disturb a user's sleep, while still maintaining high blood oxygenation accuracy and precision. Disturbing a user's sleep with uncomfortable devices is undesirable in sleep disorder screening, because the goal is to measure conditions as close as possible to the user's natural sleep habits.

A ring would also allow for general blood oxygenation monitoring throughout the day (e.g., for monitoring chronic conditions such as COPD) without obstructing a user's activities in a way a finger clip would. Other approaches rely on bulky and obtrusive devices. A ring is much less obtrusive to normal activities than this approach, and thus more suitable for all day monitoring.

In some embodiments, the system can take measurements of ambient light 707 (e.g., from the photodetectors with the light source(s) disabled). This can be used as a baseline for adjusting measurements of light from the light source(s).

The system can determine motion data using at least one motion detector on the ring 708. For example, the system can have an accelerometer, gyroscope, compass, etc. for determining whether the device is in motion. In some embodiments, this motion data can be used to determine that the device is still and ready for measurement (e.g., that a user is sleeping). The system can use measurement data to cancel out motion effects in the data. For example, oscillations manifest in the data might be caused by movement and not the user's pulse. The system can attempt to remove these effects.

The system can determine biometric information using the light information and the motion data 710. As described above, the system can use the motion data to determine periods of rest where measurements might be more reliable. The system can also use the motion data to cancel out motion effects in the data. The biometric information can be largely based on the absorption and transmission of wavelengths of light through the user's body.

The system can transmit the biometric information at the ring using a wireless protocol 712. For example, the system can use near field communication (NFC), Bluetooth, WiFi, and other protocols. In some embodiments, the system only transmits data when the user holds a phone. The system can transmit the data to a wrist device, a portable electronic device, a networked system, etc. In some embodiments, the system can relay information between devices (e.g., first to a wrist device then to a portable electronic device).

Figure 8:
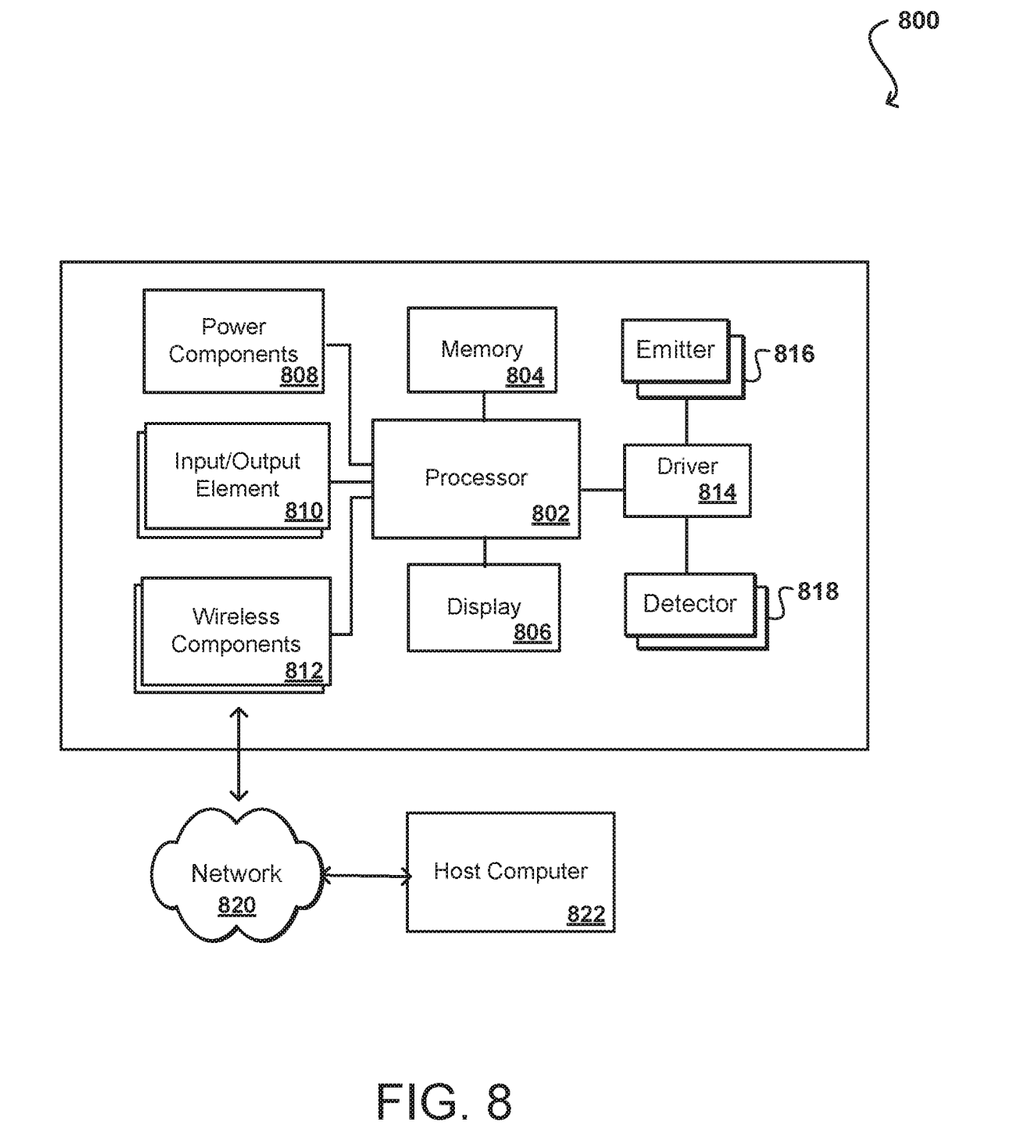
FIG. 8 illustrates components of an example computing device that can be utilized in accordance with various embodiments.

FIG. 8 illustrates components an example system that can be utilized in accordance with various embodiments. In this example, the device includes at least one processor 802, such as a central processing unit (CPU) or graphics processing unit (GPU) for executing instructions that can be stored in a memory device 804, such as may include flash memory or DRAM, among other such options. As would be apparent to one of ordinary skill in the art, the device can include many types of memory, data storage, or computer-readable media, such as data storage for program instructions for execution by a processor. The same or separate storage can be used for images or data, a removable memory can be available for sharing information with other devices, and any number of communication approaches can be available for sharing with other devices. The device typically will include some type of display 806, such as a touch screen, organic light emitting diode (OLED), or liquid crystal display (LCD), although devices might convey information via other means, such as through audio speakers or projectors.

A tracker or similar device will include at least one motion detection sensor, which as illustrated can include at least one I/O element 810 of the device. Such a sensor can determine and/or detect orientation and/or movement of the device. Such an element can include, for example, an accelerometer, inertial sensor, altimeter, or gyroscope operable to detect movement (e.g., rotational movement, angular displacement, tilt, position, orientation, motion along a non-linear path, etc.) of the device. An orientation determining element can also include an electronic or digital compass, which can indicate a direction (e.g., north or south) in which the device is determined to be pointing (e.g., with respect to a primary axis or other such aspect). A device may also include an I/O element 810 for determining a location of the device (or the user of the device). Such a positioning element can include or comprise a GPS or similar location-determining element(s) operable to determine relative coordinates for a position of the device. Positioning elements may include wireless access points, base stations, etc., that may either broadcast location information or enable triangulation of signals to determine the location of the device. Other positioning elements may include QR codes, barcodes, RFID tags, NFC tags, etc., that enable the device to detect and receive location information or identifiers that enable the device to obtain the location information (e.g., by mapping the identifiers to a corresponding location). Various embodiments can include one or more such elements in any appropriate combination. The I/O elements may also include one or more biometric sensors, optical sensors, barometric sensors (e.g., altimeter, etc.), and the like.

As mentioned above, some embodiments use the element(s) to track the location and/or motion of a user. Upon determining an initial position of a device (e.g., using GPS), the device of some embodiments may keep track of the location of the device by using the element(s), or in some instances, by using the orientation determining element(s) as mentioned above, or a combination thereof. As should be understood, the algorithms or mechanisms used for determining a position and/or orientation can depend at least in part upon the selection of elements available to the device. The example device also includes one or more wireless components 812 operable to communicate with one or more electronic devices within a communication range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections as known in the art. The device also includes one or more power components 808, such as may include a battery operable to be recharged through conventional plug-in approaches, or through other approaches such as capacitive charging through proximity with a power mat or other such device. In some embodiments the device can include at least one additional input/output device 810 able to receive conventional input from a user. This conventional input can include, for example, a push button, touch pad, touch screen, wheel, joystick, keyboard, mouse, keypad, or any other such device or element whereby a user can input a command to the device. These I/O devices could even be connected by a wireless infrared or Bluetooth or other link as well in some embodiments. Some devices also can include a microphone or other audio capture element that accepts voice or other audio commands. For example, a device might not include any buttons at all, but might be controlled only through a combination of visual and audio commands, such that a user can control the device without having to be in contact with the device.

As mentioned, many embodiments will include at least some combination of one or more emitters 816 and one or more detectors 818 for measuring data for one or more metrics of a human body, such as for a person wearing the tracker device. In some embodiments this may involve at least one imaging element, such as one or more cameras that are able to capture images of the surrounding environment and that are able to image a user, people, or objects in the vicinity of the device. The image capture element can include any appropriate technology, such as a CCD image capture element having a sufficient resolution, focal range, and viewable area to capture an image of the user when the user is operating the device. Methods for capturing images using a camera element with a computing device are well known in the art and will not be discussed herein in detail. It should be understood that image capture can be performed using a single image, multiple images, periodic imaging, continuous image capturing, image streaming, etc. Further, a device can include the ability to start and/or stop image capture, such as when receiving a command from a user, application, or other device. The example device includes emitters 816 and detectors 818 capable of being used for obtaining other biometric data, which can be used with example circuitry discussed herein.

If included, a display 806 may provide an interface for displaying data, such as HR, ECG data, blood oxygen saturation (e.g., $SpO_2$) levels, and other metrics of the user. In an embodiment, the device includes a wristband and the display is configured such that the display faces away from the outside of a user's wrist when the user wears the device. In other embodiments, the display may be omitted and data detected by the device may be transmitted using the wireless networking interface via near-field communication (NFC), Bluetooth, Wi-Fi, or other suitable wireless communication protocols over at least one network 820 to a host computer 822 for analysis, display, reporting, or other such use.

The memory 804 may comprise RAM, ROM, FLASH memory, or other non-transitory digital data storage, and may include a control program comprising sequences of instructions which, when loaded from the memory and executed using the processor 802, cause the processor 802 to perform the functions that are described herein. The emitters 816 and detectors 818 may be coupled to a bus directly or indirectly using driver circuitry by which the processor 802 may drive the light emitters 816 and obtain signals from the light detectors 818. The host computer 822 communicate with the wireless networking components 812 via one or more networks 820, which may include one or more local area networks, wide area networks, and/or internetworks using any of terrestrial or satellite links. In some embodiments, the host computer 822 executes control programs and/or application programs that are configured to perform some of the functions described herein.

In various embodiments, approaches discussed herein may be performed by one or more of: firmware operating on a monitoring or tracker device or a secondary device, such as a mobile device paired to the monitoring device, a server, host computer, and the like. For example, the monitoring device may execute operations relating to generating signals that are uploaded or otherwise communicated to a server that performs operations for removing the motion components and creating a final estimate value for physiological metrics. Alternatively, the monitoring device may execute operations relating to generating the monitoring signals and removing the motion components to produce a final estimate value for physiological metrics local to the monitoring device. In this case, the final estimate may be uploaded or otherwise communicated to a server such as host computer that performs other operations using the value.

An example monitoring or tracker device can collect one or more types of physiological and/or environmental data from one or more sensor(s) and/or external devices and communicate or relay such information to other devices (e.g., host computer or another server), thus permitting the collected data to be viewed, for example, using a web browser or network-based application. For example, while being worn by the user, a tracker device may perform biometric monitoring via calculating and storing the user's step count using one or more sensor(s). The tracker device may transmit data representative of the user's step count to an account on a web service (e.g., www.fitbit.com), computer, mobile phone, and/or health station where the data may be stored, processed, and/or visualized by the user. The tracker device may measure or calculate other physiological metric(s) in addition to, or in place of, the user's step count. Such physiological metric(s) may include, but are not limited to: energy expenditure, e.g., calorie burn; floors climbed and/or descended; HR; heartbeat waveform; HR variability; HR recovery; respiration, $SpO_2$, blood volume, blood glucose, skin moisture and skin pigmentation level, location and/or heading (e.g., via a GPS, global navigation satellite system (GLONASS), or a similar system); elevation; ambulatory speed and/or distance traveled; swimming lap count; swimming stroke type and count detected; bicycle distance and/or speed; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

An example tracker or monitoring device may also measure or calculate metrics related to the environment around the user (e.g., with one or more environmental sensor(s)), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, a tracker device (and/or the host computer and/or another server) may collect data from one or more sensors of the device, and may calculate metrics derived from such data. For example, a tracker device may calculate the user's stress or relaxation levels based on a combination of HR variability, skin conduction, noise pollution, and/or sleep quality. In another example, a tracker device may determine the efficacy of a medical intervention, for example, medication, based on a combination of data relating to medication intake, sleep, and/or activity. In yet another example, a tracker device may determine the efficacy of an allergy medication based on a combination of data relating to pollen levels, medication intake, sleep and/or activity. These examples are provided for illustration only and are not intended to be limiting or exhaustive.

An example monitoring device may include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. A monitoring system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:
1. A monitoring device, comprising:
a ring-shaped housing having an opening for receiving a digit of a person;
a plurality of light sources positioned on the ring-shaped housing and directed toward the opening, the plurality of light sources configured to emit light over at least two wavelengths;
a plurality of photodetectors positioned on the ring-shaped housing;
wherein two or more light sources selected from the plurality of light sources and two or more photodetec- tors selected from the plurality of photodetectors comprise a combination and the device comprises a plurality of combinations;
wherein the two or more light sources in the combination are configured to emit light sequentially and each of the two or more photodetectors is configured to detect light sequentially emitted along a plurality of light paths by the two or more light sources, and wherein the combination is configured to detect light that is transmitted through, and reflected from, the digit when received within the opening;
a motion-detecting element positioned in the ring-shaped housing and configured to detect motion data representative of motion of the monitoring device;
biometric circuitry positioned in the ring-shaped housing for determining biometric information using the light detected over a time period where the monitoring device is substantially still according to the detected motion data, wherein the biometric circuitry is configured to activate each combination individually; and
a communications subsystem positioned in the ring-shaped housing for communicating the biometric information using at least one wireless transmission protocol.

2. The monitoring device of claim 1, wherein the biometric circuitry is further configured to:
activate the plurality of light sources to emit light at a red wavelength and an infrared wavelength;
cause the plurality of photodetectors to detect the emitted light over a period of time;
determine a difference in absorption of the emitted light at the red wavelength and the emitted light at the infrared wavelength; and
determine, using the difference in absorption, an oxygenation level in blood of the person.

3. The monitoring device of claim 2, wherein the red wavelength is about 660 nm and the infrared wavelength is about 940 nm.

4. The monitoring device of claim 1, wherein the biometric circuitry is further configured to:
determine, using light detected over one or more wavelengths, the biometric information including at least one of blood pressure, glucose level, lipid concentration, hematocrit level, or carboxyhemoglobin level.

5. The monitoring device of claim 1, further comprising one or more opaque light barriers positioned on the ring-shaped housing for minimizing the amount of unwanted light detected by the two or more photodetectors in each combination.

6. The monitoring device of claim 1, further comprising a light guide for guiding the light paths to the two or more photodetectors in each combination.

7. The monitoring device of claim 1, further comprising an adjustment mechanism for adjusting a size of at least the opening in the ring-shaped housing.

8. A method comprising:
activating a plurality of light sources of a ring-shaped monitoring device and directed towards an opening of the ring-shaped monitoring device, wherein the plurality of light sources are configured to emit light over at least two wavelengths;
detecting, using a plurality of photodetectors of the ring-shaped monitoring device, light sequentially emitted by the plurality of light sources corresponding to a plurality of respective light paths,
wherein the two or more light sources selected from the plurality of light sources and two or more photodetectors selected from the plurality of photodetectors comprise a combination and the device comprises a plurality of combinations, wherein each combination is activated individually;
wherein two or more light sources in the combination are configured to emit light sequentially and each of the two or more photodetectors is configured to detect light sequentially emitted along a plurality of light paths by the two or more light sources, and wherein the combination is configured to detect light that is transmitted through, and reflected from, a digit of a person positioned within the opening;
determining biometric information based at least in part on differences in the detected light of the at least two wavelengths; and
transmitting the biometric information using a communications element in the ring-shaped housing.

9. The method of claim 8, further comprising:
determining, using differences in absorption of the detected light at a red wavelength and at an infrared wavelength, an oxygenation level in blood of the person.

10. The monitoring device of claim 9, wherein the red wavelength is about 660 nm and the infrared wavelength is about 940 nm.

11. The method of claim 8, further comprising:
determining, using a motion sensor, a time period over which the monitoring device is substantially still; and
determining the biometric information using light detected during the determined time period.

12. The method of claim 8, further comprising:
determining, using light detected over one or more wavelengths, the biometric information including at least one of blood pressure, glucose level, lipid concentration, or carboxyhemoglobin level.

13. The method of claim 8, wherein at least one photodetector in a combination of the device is positioned opposite at least one of the light sources in the combination in the opening.

14. The method of claim 8, further comprising:
detecting a first light intensity at a first photodetector and a second photodetector at a first location and a second location in a combination in the opening; and
detecting a second light intensity at the first photodetector and the second photodetector at the first location and the second location in the combination in the opening, wherein the biometric information is calculated based at least in part upon the first light intensity and the second light intensity.

15. The method of claim 14, wherein the first photodetector and the second photodetector in the combination are configured to receive light emitted from a same light source.

16. A wearable monitoring device, comprising:
a device housing wearable on a digit of a person;
a plurality of light sources capable of emitting light over at least a red wavelength and an infrared wavelength;
a plurality of photodetectors; wherein two or more light sources selected from the plurality of light sources and two or more photodetectors selected from the plurality of photodetectors comprise a combination and the device comprises a plurality of combinations, wherein each combination is activated individually;
wherein the two or more light sources in a combination are configured to emit light sequentially and each of the two or more photodetectors is configured for sequentially detecting light emitted along a plurality of light paths by the two or more light sources, and wherein the detected light is transmitted through, and reflected from, at least a portion of the digit of the person; and a communication subsystem configured to transmit data corresponding to differences in absorption of the red wavelength and the infrared wavelength as transmitted through, and reflected from, the portion of the digit of the finger and detected by the two or more photodetectors, the differences indicative of an oxygenation level of the person.

17. The wearable monitoring device of claim 16, further comprising:

at least one processor capable of determining the oxygenation level by calculating a relative absorption of oxygenated hemoglobin to deoxygenated hemoglobin using the absorption differences.

18. The wearable monitoring device of claim 16, further comprising at least one processor capable of determining biometric information including at least one of blood pressure, glucose level, lipid concentration, or carboxyhemoglobin level.

19. The wearable monitoring device of claim 16, wherein the device housing is a ring-shaped housing having a circular opening for at least partially receiving the digit of the person.

20. The wearable monitoring device of claim 16, further comprising:

a motion-detecting element positioned in the device housing and configured to detect motion data representative of motion of the wearable monitoring device; wherein the data corresponding to differences in absorption of the red wavelength and the infrared wavelength is collected over a time period where the monitoring device is substantially still.

* * * * *